United States Patent
Okada et al.

(10) Patent No.: US 10,126,667 B2
(45) Date of Patent: Nov. 13, 2018

(54) QUINONE DERIVATIVE AND ELECTROPHOTOGRAPHIC PHOTOSENSITIVE MEMBER

(71) Applicant: KYOCERA Document Solutions Inc., Osaka (JP)

(72) Inventors: Hideki Okada, Osaka (JP); Fumio Sugai, Osaka (JP); Kensuke Kojima, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 15/616,381

(22) Filed: Jun. 7, 2017

(65) Prior Publication Data

US 2017/0363977 A1  Dec. 21, 2017

(30) Foreign Application Priority Data

Jun. 15, 2016 (JP) .................................. 2016-118966

(51) Int. Cl.
*G03G 5/06* (2006.01)
*C07C 49/683* (2006.01)
(Continued)

(52) U.S. Cl.
CPC ......... *G03G 5/0609* (2013.01); *C07C 49/683* (2013.01); *C07C 49/697* (2013.01);
(Continued)

(58) Field of Classification Search
CPC .. G03G 5/0609; G03G 5/0618; C07C 49/683; C07C 255/56
See application file for complete search history.

(56) References Cited

U.S. PATENT DOCUMENTS

2002/0102484 A1* 8/2002 Miyamoto ........... G03G 5/0605
430/58.25

FOREIGN PATENT DOCUMENTS

JP    2000143607 A  *  5/2000
JP    2003295484 A  *  10/2003
(Continued)

OTHER PUBLICATIONS

English language machine translation of JP 2000-143607 (May 2000).*

(Continued)

*Primary Examiner* — Christopher D Rodee
(74) *Attorney, Agent, or Firm* — Studebaker & Brackett PC

(57) ABSTRACT

A quinone derivative is represented by general formula (1), (2), or (3). In general formulae (1), (2), and (3), $R^1$, $R^2$, $R^3$, $R^4$, $R^{11}$, $R^{12}$, $R^{13}$, $R^{14}$, $R^{21}$, $R^{22}$, $R^{23}$, and $R^{24}$ each represent, independently of one another, a hydrogen atom, a cyano group, a halogen atom, an optionally substituted alkyl group having a carbon number of 1-6, or an optionally substituted alkoxy group having a carbon number of 1-6. $R^5$, $R^6$, $R^{15}$, $R^{16}$, $R^{25}$, and $R^{26}$ each represent, independently of one another, an optionally substituted alkyl group having a carbon number of 1-6, an optionally substituted alkoxy group having a carbon number of 1-6, an optionally substituted aryl group having a carbon number of 6-14, an optionally substituted aralkyl group having a carbon number of 7-12, or an optionally substituted cycloalkyl group having a carbon number of 3-10.

(Continued)

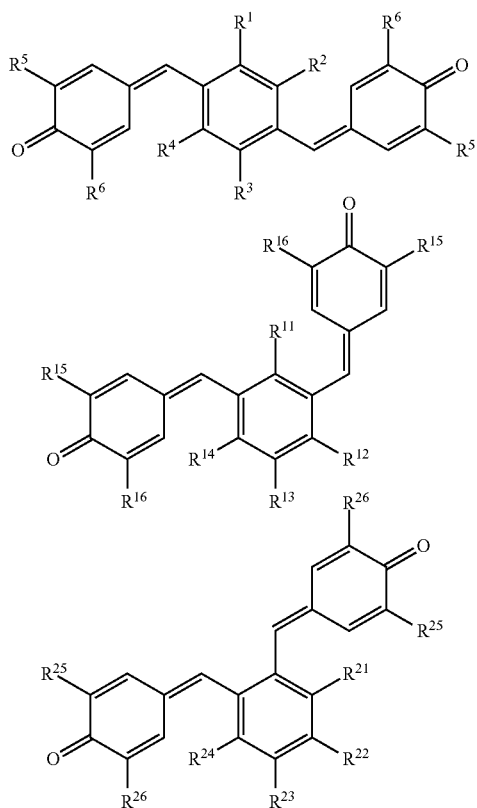

(51) Int. Cl.
 *C07C 49/697* (2006.01)
 *C07C 255/56* (2006.01)
 *G03G 5/05* (2006.01)

(52) U.S. Cl.
 CPC .......... *C07C 255/56* (2013.01); *G03G 5/0564* (2013.01); *G03G 5/0614* (2013.01); *G03G 5/0618* (2013.01); *C07C 2601/16* (2017.05)

(56) References Cited

FOREIGN PATENT DOCUMENTS

JP 2005-173292 A 6/2005
JP 2014106364 A * 6/2014

OTHER PUBLICATIONS

English language machine translation of JP 2003-295484 (Oct. 2003).*
English language machine translation of Jp 2014-106364 (Jun. 2014).*

5 Claims, 5 Drawing Sheets

* cited by examiner

QUINONE DERIVATIVE AND ELECTROPHOTOGRAPHIC PHOTOSENSITIVE MEMBER

INCORPORATION BY REFERENCE

The present application claims priority under 35 U.S.C. § 119 to Japanese Patent Application No. 2016-118966, filed on Jun. 15, 2016. The contents of this application are incorporated herein by reference in their entirety.

BACKGROUND

The present disclosure relates to quinone derivatives and electrophotographic photosensitive members.

An electrophotographic photosensitive member is used in an electrophotographic image forming apparatus. The electrophotographic photosensitive member includes a photosensitive layer. The electrophotographic photosensitive member is for example a multi-layer electrophotographic photosensitive member or a single-layer electrophotographic photosensitive member. The multi-layer electrophotographic photosensitive member includes, as the photosensitive layer thereof, a charge generating layer having a charge generating function and a charge transport layer having a charge transport function. The single-layer electrophotographic photosensitive member includes, as the photosensitive layer thereof, a single-layer photosensitive layer having a charge generating function and a charge transport function.

An electrophotographic photosensitive member shown below is known. A photosensitive layer of the electrophotographic photosensitive member for example contains a compound represented by chemical formula (E-1) or (E-2).

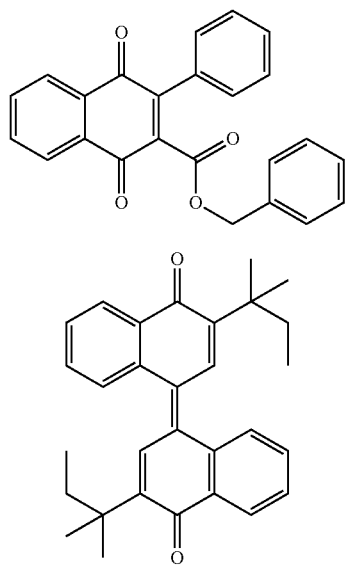

SUMMARY

A quinone derivative according to an aspect of the present disclosure is represented by general formula (1), (2), or (3) shown below.

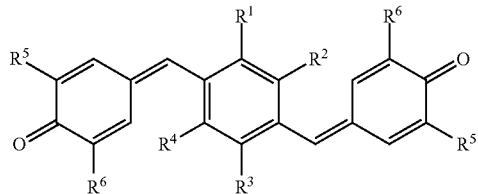

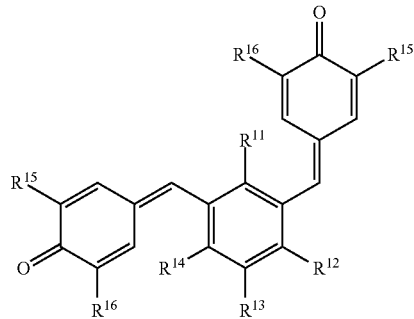

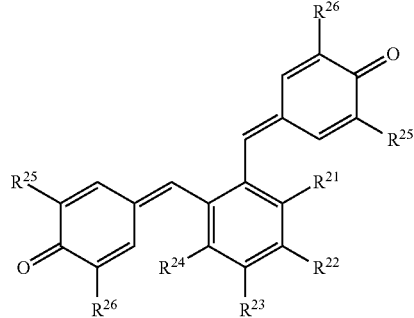

In general formulae (1), (2), and (3), $R^1$, $R^2$, $R^3$, $R^4$, $R^{11}$, $R^{12}$, $R^{13}$, $R^{14}$, $R^{21}$, $R^{22}$, $R^{23}$, and $R^{24}$ each represent, independently of one another, a hydrogen atom, a cyano group, a halogen atom, an optionally substituted alkyl group having a carbon number of at least 1 and no greater than 6, or an optionally substituted alkoxy group having a carbon number of at least 1 and no greater than 6. $R^5$, $R^6$, $R^{15}$, $R^{16}$, $R^{25}$, and $R^{26}$ each represent, independently of one another, an optionally substituted alkyl group having a carbon number of at least 1 and no greater than 6, an optionally substituted alkoxy group having a carbon number of at least 1 and no greater than 6, an optionally substituted aryl group having a carbon number of at least 6 and no greater than 14, an optionally substituted aralkyl group having a carbon number of at least 7 and no greater than 12, or an optionally substituted cycloalkyl group having a carbon number of at least 3 and no greater than 10.

An electrophotographic photosensitive member according to an aspect of the present disclosure includes a conductive substrate and a photosensitive layer. The photosensitive layer contains a charge generating material, a hole transport material, the above-described quinone derivative, and a binder resin.

DETAILED DESCRIPTION

Figure 1A:
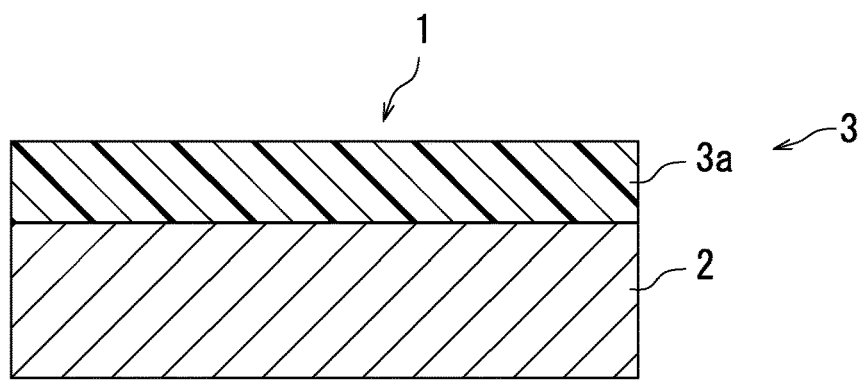
FIGS. 1A, 1B, and 1C are schematic cross-sectional views each illustrating an example of an electrophotographic photosensitive member according to a second embodiment of the present disclosure.

The following describes embodiments of the present disclosure in detail. The present disclosure is not in any way limited by the following embodiments. Appropriate changes may be made when practicing the present disclosure so long as such changes do not deviate from the intended scope of the present disclosure. Although description is omitted in some places in order to avoid repetition, such omission does not limit the essence of the present disclosure.

In the present specification, the term "-based" may be appended to the name of a chemical compound in order to form a generic name encompassing both the chemical compound itself and derivatives thereof. When the term "-based" is appended to the name of a chemical compound used in the name of a polymer, the term indicates that a repeating unit of the polymer originates from the chemical compound or a derivative thereof.

In the present specification, an alkyl group having a carbon number of at least 1 and no greater than 6, an alkyl group having a carbon number of at least 1 and no greater than 4, an alkyl group having a carbon number of at least 1 and no greater than 3, an alkoxy group having a carbon number of at least 1 and no greater than 6, an aryl group having a carbon number of at least 6 and no greater than 14, an aralkyl group having a carbon number of at least 7 and no greater than 12, a cycloalkyl group having a carbon number of at least 3 and no greater than 10, a halogen atom, and a heterocyclic group each refer to the following unless otherwise stated.

An alkyl group having a carbon number of at least 1 and no greater than 6 as used herein refers to an unsubstituted straight chain or branched chain alkyl group. Examples of the alkyl group having a carbon number of at least 1 and no greater than 6 include a methyl group, an ethyl group, an n-propyl group, an isopropyl group, an n-butyl group, an s-butyl group, a t-butyl group, a pentyl group, an isopentyl group, a neopentyl group, and an n-hexyl group.

An alkyl group having a carbon number of at least 1 and no greater than 4 as used herein refers to an unsubstituted straight chain or branched chain alkyl group. Examples of the alkyl group having a carbon number of at least 1 and no greater than 4 include a methyl group, an ethyl group, an n-propyl group, an isopropyl group, an n-butyl group, an s-butyl group, and a t-butyl group.

An alkyl group having a carbon number of at least 1 and no greater than 3 as used herein refers to an unsubstituted straight chain or branched chain alkyl group. Examples of the alkyl group having a carbon number of at least 1 and no greater than 3 include a methyl group, an ethyl group, an n-propyl group, and an isopropyl group.

An alkoxy group having a carbon number of at least 1 and no greater than 6 as used herein refers to an unsubstituted straight chain or branched chain alkyl group. Examples of the alkoxy group having a carbon number of at least 1 and no greater than 6 include a methoxy group, an ethoxy group, an n-propoxy group, an isopropoxy group, an n-butoxy group, an s-butoxy group, a t-butoxy group, a pentoxy group, and a hexyloxy group.

An aryl group having a carbon number of at least 6 and no greater than 14 as used herein refers to an unsubstituted aryl group. An aryl group having a carbon number of at least 6 and no greater than 14 as used herein is for example an unsubstituted monocyclic aromatic hydrocarbon group having a carbon number of at least 6 and no greater than 14, an unsubstituted fused bicyclic aromatic hydrocarbon group having a carbon number of at least 6 and no greater than 14, or an unsubstituted fused tricyclic aromatic hydrocarbon group having a carbon number of at least 6 and no greater than 14. Examples of the aryl group having a carbon number of at least 6 and no greater than 14 include a phenyl group, a naphthyl group, an anthryl group, and a phenanthryl group.

An aralkyl group having a carbon number of at least 7 and no greater than 12 as used herein refers to an unsubstituted straight chain or branched chain aralkyl group. An aralkyl group having a carbon number of at least 7 and no greater than 12 is for example a group formed through bonding of a phenyl group with an alkyl group having a carbon number of at least 1 and no greater than 6 or a group formed through bonding of a naphthyl group with a methyl group or an ethyl group.

A cycloalkyl group having a carbon number of at least 3 and no greater than 10 as used herein refers to an unsubstituted cycloalkyl group. Examples of the cycloalkyl group having a carbon number of at least 3 and no greater than 10 include a cyclopropyl group, a cyclobutyl group, a cyclopentyl group, a cyclohexyl group, a cycloheptyl group, a cyclooctyl group, a cyclononyl group, and a cyclodecyl group.

A halogen atom as used herein for example refers to a fluorine atom, a chlorine atom, a bromine atom, or an iodine atom.

A heterocyclic group as used herein refers to an unsubstituted heterocyclic group. Examples of the heterocyclic group include a heterocyclic group formed by a five- or six-membered aromatic monocyclic ring including at least one (preferably, at least 1 and no greater than 3) hetero atom; a heterocyclic group formed by such monocyclic rings fused together; and a heterocyclic group formed by such a monocyclic ring and a five- or six-membered hydrocarbon ring fused together. The hetero atom is at least one atom selected from the group consisting of a nitrogen atom, a sulfur atom, and an oxygen atom. Specific examples of heterocyclic groups include a thiophenyl group, a furanyl group, a pyrrolyl group, an imidazolyl group, a pyrazolyl group, isothiazolyl group, an isoxazolyl group, an oxazolyl group, a thiazolyl group, a furazanyl group, a pyranyl group, a pyridyl group, a pyridazinyl group, a pyrimidinyl group, a pyrazinyl group, an indolyl group, a 1H-indazolyl group, an isoindolyl group, a chromenyl group, a quinolinyl group, an isoquinolinyl group, a purinyl group, a pteridinyl group, a triazolyl group, a tetrazolyl group, a 4H-quinolizinyl group, a naphthyridinyl group, a benzofuranyl group, a 1,3-benzodioxolyl group, a benzoxazolyl group, a benzothiazolyl group, and a benzimidazolyl group.

<First Embodiment: Quinone Derivative>
<1. Quinone Derivative>

A first embodiment of the present disclosure relates to quinone derivatives. The quinone derivatives according to the first embodiment are represented by general formulae (1), (2), and (3). Hereinafter, the quinone derivatives represented by general formulae (1), (2), and (3) may be respectively referred to as quinone derivatives (1), (2), and (3).

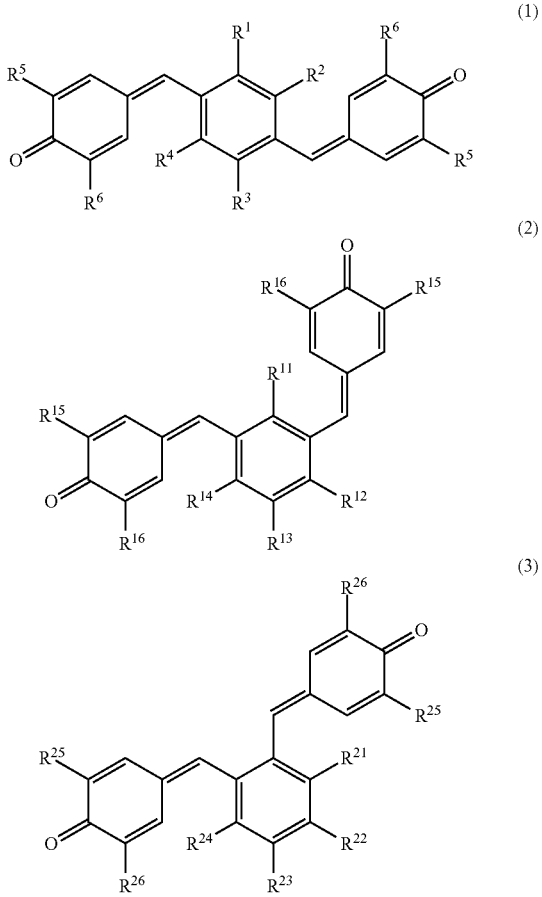

In the general formulae (1), (2), and (3), $R^1$, $R^2$, $R^3$, and $R^4$ (also referred to below as $R^1$ to $R^4$), $R^{11}$, $R^{12}$, $R^{13}$, and $R^{14}$ (also referred to below as $R^{11}$ to $R^{14}$), and $R^{21}$, $R^{22}$, $R^{23}$, and $R^{24}$ (also referred to below as $R^{21}$ to $R^{24}$) each represent, independently of one another, a hydrogen atom, a cyano group, a halogen atom, an optionally substituted alkyl group having a carbon number of at least 1 and no greater than 6, or an optionally substituted alkoxy group having a carbon number of at least 1 and no greater than 6. $R^5$ and $R^6$ (also referred to below as $R^5$ to $R^6$), $R^{15}$ and $R^{16}$ (also referred to below as $R^{15}$ to $R^{16}$), and $R^{25}$ and $R^{26}$ (also referred to below as $R^{25}$ to $R^{26}$) each represent, independently of one another, an optionally substituted alkyl group having a carbon number of at least 1 and no greater than 6, an optionally substituted alkoxy group having a carbon number of at least 1 and no greater than 6, an optionally substituted aryl group having a carbon number of at least 6 and no greater than 14, an optionally substituted aralkyl group having a carbon number of at least 7 and no greater than 12, or an optionally substituted cycloalkyl group having a carbon number of at least 3 and no greater than 10.

Contained in an electrophotographic photosensitive member (also referred to below simply as a photosensitive member), the quinone derivatives (1), (2), and (3) according to the first embodiment improve electrical characteristics of the electrophotographic photosensitive member. The reason for the above is thought to be as follows. The following description takes the quinone derivative (1) as an example. The quinone derivative (1) has a structure in which two benzoquinone methide moieties are bonded to a benzene ring. Thus, the quinone derivative (1) has a relatively large π-conjugated system, and therefore tends to have excellent carrier (electron) accepting and transporting abilities. In the quinone derivative (1), the benzoquinone methide moieties each have $R^5$ and $R^6$, the benzene ring has $R^1$, $R^2$, $R^3$, and $R^4$, and the bonds (single bonds) between the benzene ring and the benzoquinone methide moieties may rotate. The quinone derivative (1) therefore tends to have excellent solubility in a solvent for formation of a photosensitive layer and excellent dispersibility in the photosensitive layer. Like the quinone derivative (1), the quinone derivatives (2) and (3) also have excellent carrier accepting and transporting abilities, excellent solubility in a solvent for formation of a photosensitive layer, and excellent dispersibility in the photosensitive layer. It is therefore thought that the quinone derivatives (1), (2), and (3) according to the first embodiment improve electrical characteristics of the photosensitive member.

The following continues description of the quinone derivatives (1), (2), and (3) according to the first embodiment. The halogen atom represented by any of $R^1$ to $R^4$, $R^{11}$ to $R^{14}$, and $R^{21}$ to $R^{24}$ in general formulae (1), (2), and (3) is preferably a chlorine atom.

The alkyl group having a carbon number of at least 1 and no greater than 6 represented by any of $R^1$ to $R^4$, $R^{11}$ to $R^{14}$, and $R^{21}$ to $R^{24}$ in general formulae (1), (2), and (3) is preferably an alkyl group having a carbon number of at least 1 and no greater than 3, and more preferably a methyl group. The alkyl group having a carbon number of at least 1 and no greater than 6 represented by any of $R^5$ to $R^6$, $R^{15}$ to $R^{16}$, and $R^{25}$ to $R^{26}$ in general formulae (1), (2), and (3) is preferably an alkyl group having a carbon number of at least 1 and no greater than 4, and more preferably a methyl group or a t-butyl group. The alkyl group having a carbon number of at least 1 and no greater than 6 represented by any of $R^1$ to $R^6$, $R^{11}$ to $R^{16}$, and $R^{21}$ to $R^{26}$ may optionally have a substituent. Examples of possible substituents include a halogen atom, an alkoxy group having a carbon number of at least 1 and no greater than 6, a cycloalkyl group having a carbon number of at least 3 and no greater than 10, and a heterocyclic group.

The alkoxy group having a carbon number of at least 1 and no greater than 6 represented by any of $R^1$ to $R^6$, $R^{11}$ to $R^{16}$, and $R^{21}$ to $R^{26}$ in general formulae (1), (2), and (3) may optionally have a substituent. Examples of possible substituents include a halogen atom, an alkoxy group having a carbon number of at least 1 and no greater than 6, an aryl group having a carbon number of at least 6 and no greater than 14, a cycloalkyl group having a carbon number of at least 3 and no greater than 10, and a heterocyclic group.

The aryl group having a carbon number of at least 6 and no greater than 14 represented by any of $R^5$ to $R^6$, $R^{15}$ to $R^{16}$, and $R^{25}$ to $R^{26}$ in general formulae (1), (2), and (3) may optionally have a substituent. Examples of possible substituents include a halogen atom, an alkyl group having a carbon number of at least 1 and no greater than 6, an alkoxy group having a carbon number of at least 1 and no greater than 6, an aryl group having a carbon number of at least 6 and no greater than 14, a cycloalkyl group having a carbon number of at least 3 and no greater than 10, and a heterocyclic group.

The aralkyl group having a carbon number of at least 6 and no greater than 12 represented by any of $R^5$ to $R^6$, $R^{15}$ to $R^{16}$, and $R^{25}$ to $R^{26}$ in general formulae (1), (2), and (3) may optionally have a substituent. Examples of possible substituents include a halogen atom, an alkyl group having a carbon number of at least 1 and no greater than 6, an alkoxy group having a carbon number of at least 1 and no greater than 6, an aryl group having a carbon number of at least 6 and no greater than 14, a cycloalkyl group having a carbon number of at least 3 and no greater than 10, and a heterocyclic group.

The cycloalkyl group having a carbon number of at least 3 and no greater than 10 represented by any of $R^5$ to $R^6$, $R^{15}$ to $R^{16}$, and $R^{25}$ to $R^{26}$ in general formulae (1), (2), and (3) may optionally have a substituent. Examples of possible substituents include a halogen atom, an alkyl group having a carbon number of at least 1 and no greater than 6, an alkoxy group having a carbon number of at least 1 and no greater than 6, an aryl group having a carbon number of at least 6 and no greater than 14, a cycloalkyl group having a carbon number of at least 3 and no greater than 10, and a heterocyclic group.

Preferably, in general formulae (1), (2), and (3), $R^1$ to $R^4$, $R^{11}$ to $R^{14}$, and $R^{21}$ to $R^{24}$ each represent, independently of one another, a hydrogen atom, a cyano group, a halogen atom, or an alkyl group having a carbon number of at least 1 and no greater than 3 $R^5$ to $R^6$, $R^{15}$ to $R^{16}$, and $R^{25}$ to $R^{26}$ each represent, independently of one another, an alkyl group having a carbon number of at least 1 and no greater than 4 (more preferably, a methyl group or a t-butyl group), the two chemical groups $R^5$ are the same as one another, the two chemical groups $R^6$ are the same as one another, the two chemical groups $R^{15}$ are the same as one another, the two chemical groups $R^{16}$ are the same as one another, the two chemical groups $R^{25}$ are the same as one another, and the two chemical groups $R^{26}$ are the same as one another.

In terms of costs and in terms of further improving electrical characteristics of the photosensitive member, $R^1$ to $R^4$, $R^{11}$ to $R^{14}$, and $R^{21}$ to $R^{24}$ in general formulae (1), (2), and (3) are each preferably a hydrogen atom.

All the chemical groups $R^1$ to $R^4$ in general formula (1) may or may not be the same as one another. All the chemical groups $R^1$ to $R^4$ not being the same as one another means at least one of $R^1$ to $R^4$ being different from the others. $R^5$ to $R^6$ in general formula (1) may be the same as or different from one another. The two chemical groups $R^5$ in general formula (1) may be the same as or different from one another. The two chemical groups $R^6$ may be the same as or different from one another. The quinone derivative (1) can lose its symmetry when all the chemical groups $R^1$ to $R^4$ in general formula (1) are not the same as one another, when $R^5$ to $R^6$ are different from one another, when the two chemical groups $R^5$ are different from one another, or when the two chemical groups $R^6$ are different from one another.

All the chemical groups $R^{11}$ to $R^{14}$ in general formula (2) may or may not be the same as one another. All the chemical groups $R^{11}$ to $R^{14}$ not being the same as one another means at least one of $R^{11}$ to $R^{14}$ being different from the others. $R^{15}$ to $R^{16}$ in general formula (2) may be the same as one another or different from one another. The two chemical groups $R^{15}$ in general formula (2) may be the same as or different from one another. The two chemical groups $R^{16}$ may be the same as or different from one another. The quinone derivative (2) can lose its symmetry when all the chemical groups $R^{11}$ to $R^{14}$ in general formula (2) are not the same as one another, when $R^{15}$ to $R^{16}$ are different from one another, when the two chemical groups $R^{15}$ are different from one another, or when the two chemical groups $R^{16}$ are different from one another.

$R^{21}$ to $R^{24}$ in general formula (3) may or may not be the same as one another. All the chemical groups $R^{21}$ to $R^{24}$ not being the same as one another means at least one of $R^{21}$ to $R^{24}$ being different from the others. $R^{25}$ to $R^{26}$ in general formula (3) may be the same as or different from one another. The two chemical groups $R^{25}$ in general formula (3) may be the same as or different from one another. The two chemical groups $R^{26}$ may be the same as or different from one another. The quinone derivative (3) can lose its symmetry when all the chemical groups $R^{21}$ to $R^{24}$ in general formula (3) are not the same as one another, when $R^{25}$ to $R^{26}$ are different from one another, when the two chemical groups $R^{25}$ are different from one another, or when the two chemical groups $R^{26}$ are different from one another.

Specific examples of the quinone derivative (1) include quinone derivatives represented by chemical formulae (1-1) to (1-6) (also respectively referred to below as quinone derivatives (1-1) to (1-6)).

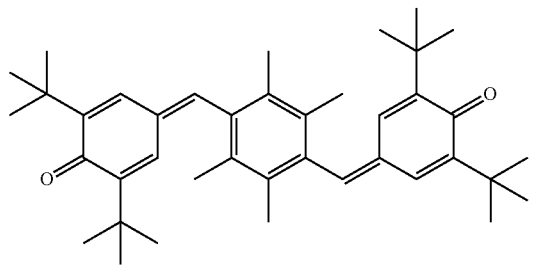

(1-1)

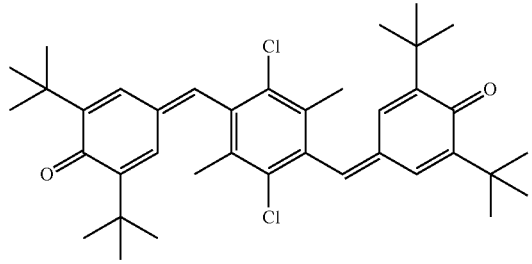

(1-2)

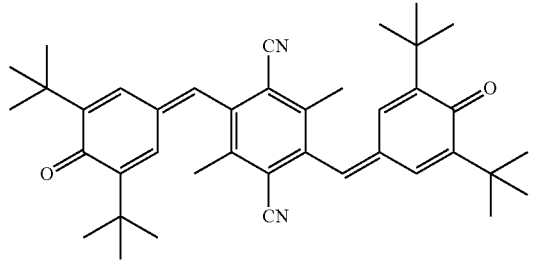

(1-3)

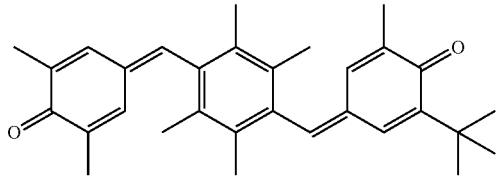

(1-4)

-continued (1-5)
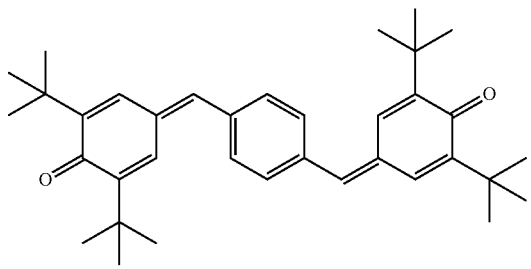

(1-6)
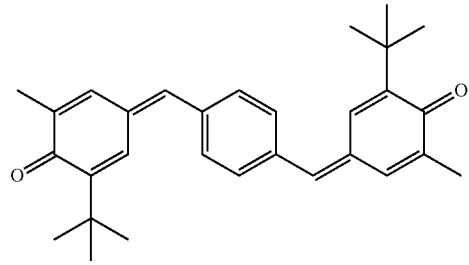

Specific examples of the quinone derivative (2) include a quinone derivative represented by chemical formula (2-1) (also referred to below as a quinone derivative (2-1)).

(2-1)
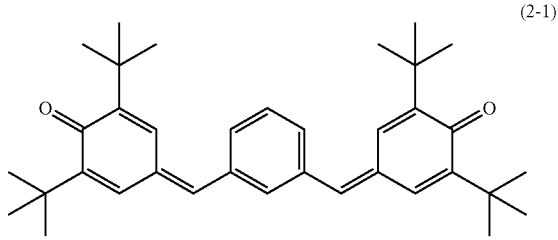 [SMILES: CC(C)(C)C1=CC(=Cc2cccc(C=C3C=C(C(C)(C)C)C(=O)C(C(C)(C)C)=C3)c2)C=C(C(C)(C)C)C1=O]

Specific examples of the quinone derivative (3) include a quinone derivative represented by chemical formula (3-1).

(3-1)
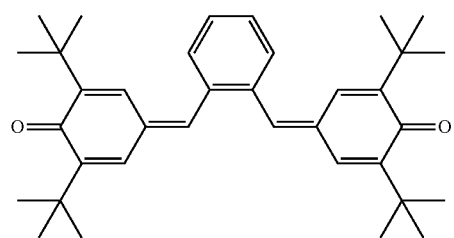

<2. Method for Producing Quinone Derivative>

[2-1. Method for Producing Quinone Derivative (1)]

The quinone derivative (1) is for example produced through a reaction represented by reaction formula (R-1) (also referred to below as a reaction (R-1)) or through a method conforming therewith. The method for producing the quinone derivative (1) for example involves the reaction (R-1).

In the reaction (R-1), $R^1$ to $R^6$ in general formula (A1) respectively represent the same as $R^1$ to $R^6$ in general formula (1).

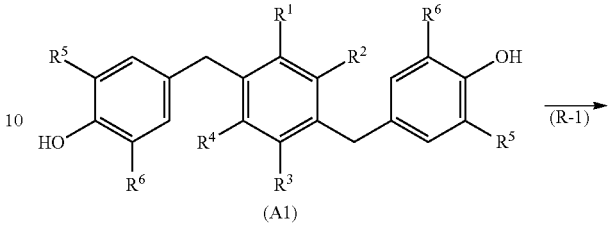

(A1)

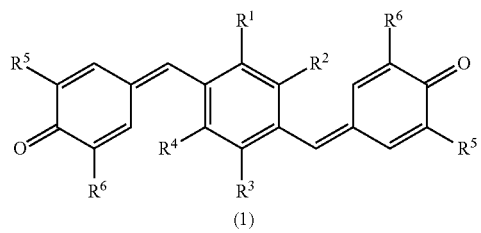

(1)

In the reaction (R-1), one equivalent of a phenol derivative represented by general formula (A1) (also referred to below as a phenol derivative (A1)) is caused to react in a solvent in the presence of an oxidant to yield one equivalent of the quinone derivative (1). Preferably, in the reaction (R-1), at least 20 moles and no greater than 40 moles of the oxidant is added to one mole of the phenol derivative (A1). As a result of at least 20 moles of the oxidant being added to the phenol derivative (A1) in an amount of one mole, the quinone derivative (1) is easily produced with a high percentage yield. As a result of no greater than 40 moles of the oxidant being added to the phenol derivative (A1) in an amount of one mole, the oxidant tends not to remain unreacted in the reaction, enabling easy purification of the quinone derivative (1). Preferably, a reaction time of the reaction (R-1) is at least 5 hours and no greater than 30 hours. Preferably, a reaction temperature of the reaction (R-1) is at least 10° C. and no greater than 50° C. Examples of solvents that can be used include chloroform and dichloromethane. Examples of oxidants that can be used include potassium permanganate, hydrogen peroxide, meta-chloroperbenzoic acid, and preoxyacetic acid.

The production of the quinone derivative (1) may include an optional step (for example, purification step) as necessary. The optional step is for example a purification step. Examples of purification methods that can be employed include known methods (specific examples include filtration, chromatography, and crystallization).

[2-2. Method for Producing Quinone Derivative (2)]

The quinone derivative (2) is for example produced through a reaction represented by reaction formula (R-2) (also referred to below as a reaction (R-2)) or through a method conforming therewith. The method for producing the quinone derivative (2) for example involves the reaction (R-2).

In the reaction (R-2), $R^{11}$ to $R^{16}$ in general formula (A2) respectively represent the same as $R^{11}$ to $R^{16}$ in general formula (2).

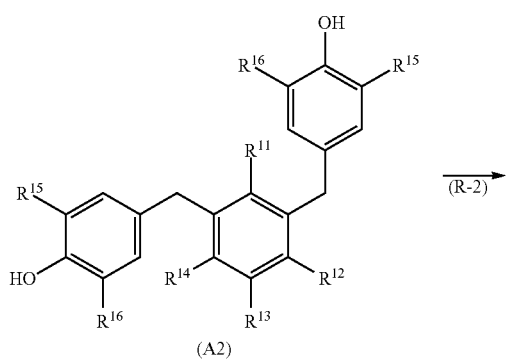

(A2)

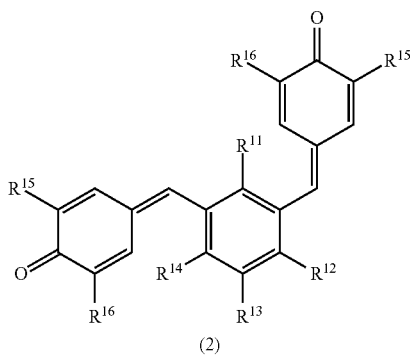

(2)

The reaction (R-2) is the same reaction as the reaction (R-1) except that a phenol derivative represented by general formula (A2) (also referred to below as a phenol derivative (A2)) is used instead of the phenol derivative (A1).

[2-3. Method for Producing Quinone Derivative (3)]

The quinone derivative (3) is for example produced through a reaction represented by reaction formula (R-3) (also referred to below as a reaction (R-3)) or through a method conforming therewith. The method for producing the quinone derivative (3) for example involves the reaction (R-3).

In the reaction (R-3), $R^{21}$ to $R^{26}$ in general formula (A3) respectively represent the same as $R^{21}$ to $R^{26}$ in general formula (3).

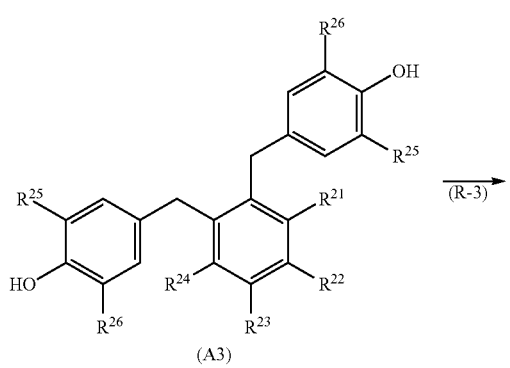

(A3)

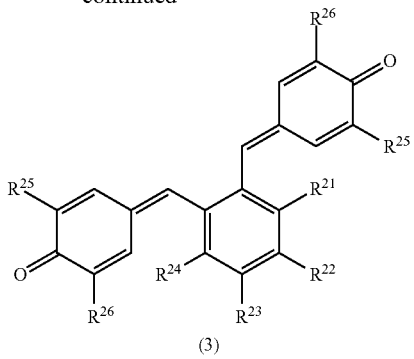

(3)

The reaction (R-3) is the same reaction as the reaction (R-1) except that a phenol derivative represented by general formula (A3) is used instead of the phenol derivative (A1).

Through the above, the quinone derivatives (1), (2), and (3) according to the first embodiment have been described. The quinone derivatives (1), (2), and (3) according to the first embodiment improve electrical characteristics of the photosensitive member.

<Second Embodiment: Electrophotographic Photosensitive Member>

A second embodiment of the present disclosure relates to photosensitive members. Examples of photosensitive members include a single-layer electrophotographic photosensitive member (also referred to below simply as a single-layer photosensitive member) and a multi-layer electrophotographic photosensitive member (also referred to below simply as a multi-layer photosensitive member).

<1. Single-Layer Photosensitive Member>

Figure 1B:
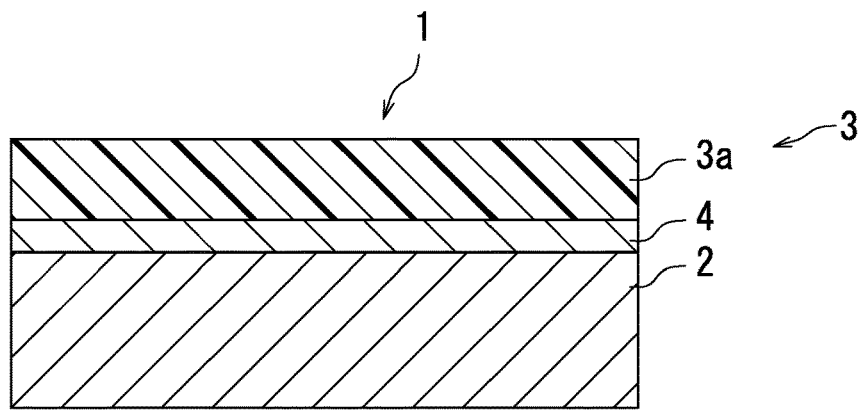
Figure 1C:
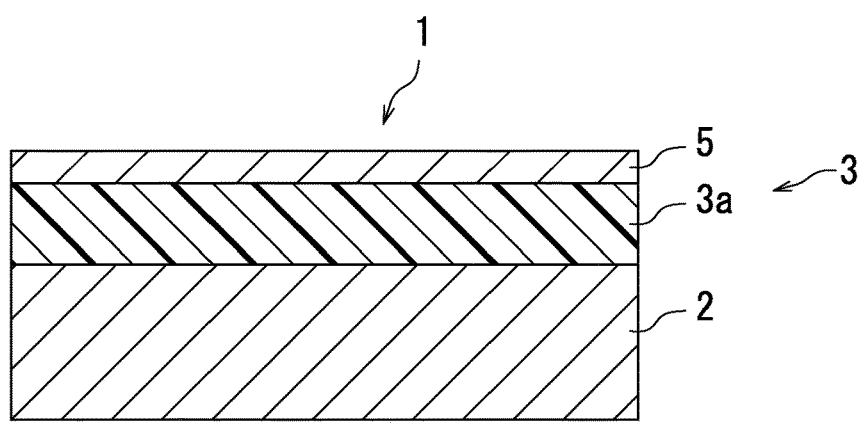

The following describes a structure of a photosensitive member 1 in the form of a single-layer photosensitive member with reference to FIGS. 1A to 1C. FIGS. 1A to 1C are schematic cross-sectional views each illustrating a single-layer photosensitive member as an example of the photosensitive member 1 according to the second embodiment.

As illustrated in FIG. 1A, the single-layer photosensitive member serving as the photosensitive member 1 includes a conductive substrate 2 and a photosensitive layer 3. The single-layer photosensitive member serving as the photosensitive member 1 includes a single-layer photosensitive layer 3a as the photosensitive layer 3. The single-layer photosensitive layer 3a is a one-layer photosensitive layer 3.

The single-layer photosensitive member serving as the photosensitive member 1 may include the conductive substrate 2, the single-layer photosensitive layer 3a, and an intermediate layer (undercoat layer) 4 as illustrated in FIG. 1B. The intermediate layer 4 is provided between the conductive substrate 2 and the single-layer photosensitive layer 3a. A protective layer 5 may be provided on the single-layer photosensitive layer 3a as illustrated in FIG. 1C.

No particular limitations are placed on thickness of the single-layer photosensitive layer 3a so long as the thickness thereof is sufficient to enable the single-layer photosensitive layer 3a to function as a single-layer photosensitive layer. The single-layer photosensitive layer 3a preferably has a thickness of at least 5 μm and no greater than 100 μm, and more preferably at least 10 μm and no greater than 50 μm.

The single-layer photosensitive layer 3a serving as the photosensitive layer 3 contains a charge generating material, a hole transport material, the quinone derivative (1), (2), or (3) serving as an electron transport material, and a binder resin. The single-layer photosensitive layer 3a may optionally contain various additives. That is, the single-layer photosensitive member serving as the photosensitive member 1 contains a charge generating material, a hole transport material, the quinone derivative (1), (2), or (3) serving as an electron transport material, a binder resin, and a component that is added as necessary (for example, an additive) in the one-layer photosensitive layer 3 (single-layer photosensitive layer 3a). Through the above, the structure of the photosensitive member 1 in the form of a single-layer photosensitive member has been described with reference to FIGS. 1A to 1C.

<2. Multi-Layer Photosensitive Member>

Figure 2A:
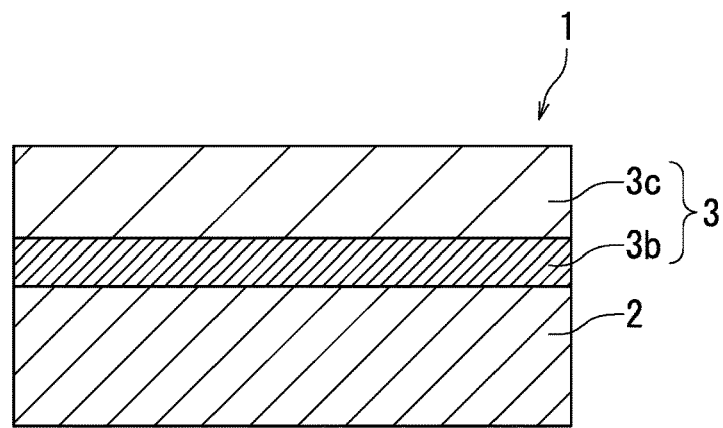
FIGS. 2A, 2B, and 2C are schematic cross-sectional views each illustrating another example of the electrophotographic photosensitive member according to the second embodiment of the present disclosure.
Figure 2B:
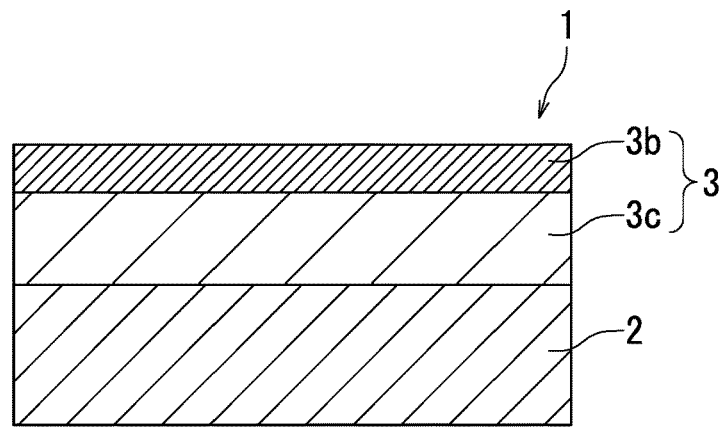
Figure 2C:
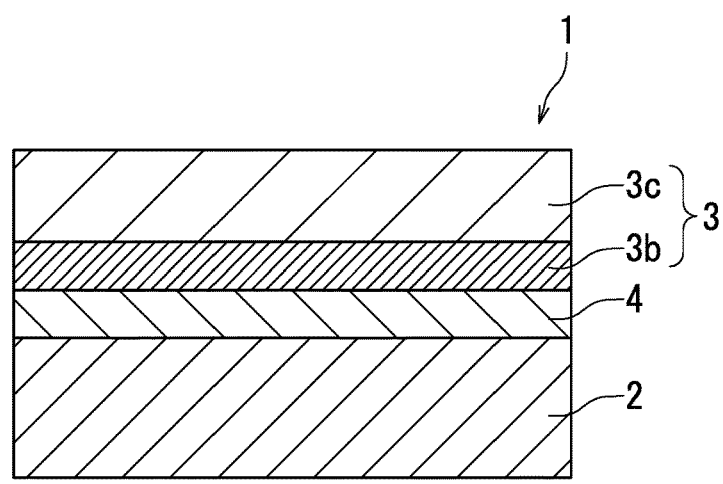

The following describes a structure of the photosensitive member 1 in the form of a multi-layer photosensitive member with reference to FIGS. 2A to 2C. FIGS. 2A to 2C are schematic cross-sectional views each illustrating a multi-layer photosensitive member as an example of the photosensitive member 1 according to the second embodiment.

As illustrated in FIG. 2A, the multi-layer photosensitive member serving as the photosensitive member 1 includes the conductive substrate 2 and the photosensitive layer 3. The photosensitive layer 3 includes a charge generating layer 3b and a charge transport layer 3c. In order to improve abrasion resistance of the multi-layer photosensitive member, it is preferable to provide the charge generating layer 3b on the conductive substrate 2 and provide the charge transport layer 3c on the charge generating layer 3b as illustrated in FIG. 2A.

The charge transport layer 3c may be provided on the conductive substrate 2 and the charge generating layer 3b may be provided on the charge transport layer 3c in the multi-layer photosensitive member serving as the photosensitive member 1 as illustrated in FIG. 2B.

As illustrated in FIG. 2C, the multi-layer photosensitive member serving as the photosensitive member 1 may include the conductive substrate 2, the photosensitive layer 3, and the intermediate layer (undercoat layer) 4. The intermediate layer 4 is provided between the conductive substrate 2 and the photosensitive layer 3. The protective layer 5 may be further provided on the photosensitive layer 3 (see FIG. 1C).

No particular limitations are placed on thickness of the charge generating layer 3b and the charge transport layer 3c so long as the thicknesses thereof are sufficient to enable the charge generating layer 3b and the charge transport layer 3c to implement the respective functions thereof. The charge generating layer 3b preferably has a thickness of at least 0.01 µm and no greater than 5 µm, and more preferably at least 0.1 µm and no greater than 3 µm. The charge transport layer 3c preferably has a thickness of at least 2 µm and no greater than 100 µm, and more preferably at least 5 µm and no greater than 50 µm.

The charge generating layer 3b in the photosensitive layer 3 for example contains a charge generating material and a charge generating layer binder resin (also referred to below as a base resin). The charge generating layer 3b may optionally contain various additives.

The charge transport layer 3c for example contains a hole transport material, the quinone derivative (1), (2), or (3) as an electron acceptor compound, and a binder resin. The charge transport layer 3c may optionally contain various additives. Through the above, the structure of the photosensitive member 1 in the form of a multi-layer photosensitive member has been described with reference to FIGS. 2A to 2C.

The following describes elements of the multi-layer photosensitive member and the single-layer photosensitive member.

<3. Conductive Substrate>

No specific limitations are placed on the conductive substrate other than being a conductive substrate that can be used in photosensitive members. The conductive substrate can be a conductive substrate of which at least a surface portion thereof is made from a conductive material. For example, the conductive substrate is a conductive substrate made from a conductive material. For another example, the conductive substrate is a conductive substrate having a conductive material coating. Examples of conductive materials that can be used include aluminum, iron, copper, tin, platinum, silver, vanadium, molybdenum, chromium, cadmium, titanium, nickel, palladium, and indium. Any one of the conductive materials listed above may be used independently, or any two or more of the conductive materials listed above may be used in combination. Examples of combinations of two or more of the conductive materials include an alloy (specific examples include an aluminum alloy, stainless steel, and brass). Of the conductive materials listed above, aluminum or an aluminum alloy is preferable in terms of favorable charge mobility from the photosensitive layer to the conductive substrate.

The shape of the conductive substrate may be selected as appropriate to match the structure of an image forming apparatus in which the conductive substrate is to be used. The conductive substrate is for example a sheet-shaped conductive substrate or a drum-shaped conductive substrate. The thickness of the conductive substrate is selected as appropriate in accordance with the shape of the conductive substrate.

<4. Electron Transport Material, Electron Acceptor Compound>

As already described, in the case of the multi-layer photosensitive member, the charge transport layer contains the quinone derivative (1), (2), or (3) as an electron acceptor compound. In the case of the single-layer photosensitive member, the single-layer photosensitive layer contains the quinone derivative (1), (2), or (3) as an electron transport material. As a result of the photosensitive layer containing the quinone derivative (1), (2), or (3), the photosensitive member according to the second embodiment has excellent electrical characteristics.

In the case of the multi-layer photosensitive member, the quinone derivative (1), (2), or (3) is preferably contained in an amount of at least 10 parts by mass and no greater than 200 parts by mass relative to 100 parts by mass of the binder resin contained in the charge transport layer, and more preferably at least 20 parts by mass and no greater than 100 parts by mass.

In the case of the single-layer photosensitive member, the quinone derivative (1), (2), or (3) is preferably contained in an amount of at least 10 parts by mass and no greater than 200 parts by mass relative to 100 parts by mass of the binder resin contained in the single-layer photosensitive layer, and more preferably at least 10 parts by mass and no greater than 100 parts by mass, and particularly preferably at least 10 parts by mass and no greater than 75 parts by mass.

The charge transport layer may contain an additional electron acceptor compound besides the quinone derivative (1), (2), or (3). The single-layer photosensitive layer may contain an additional electron transport material besides the quinone derivative (1), (2), or (3). Examples of electron acceptor compounds and electron transport materials that can be additionally used include quinone-based compounds other than the quinone derivatives (1), (2), and (3), diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydridem, and dibromomaleic anhydride. Examples of quinone-based compounds that can be used include diphenoquinone-based compounds, azoquinone-based compounds, anthraquinone-based compounds, naphthoquinone-based compounds, nitroanthraquinone-based compounds, and dinitroanthraquinone-based compounds. Any one of the electron transport materials listed above may be used independently, or any two or more of the electron transport materials listed above may be used in combination.

<5. Hole Transport Material>

Examples of hole transport materials that can be used include nitrogen-containing cyclic compounds and condensed polycyclic compounds. Examples of nitrogen-containing cyclic compounds and condensed polycyclic compounds that can be used include diamine derivatives (specific examples include N,N,N',N'-tetraphenylphenylenediamine derivatives, N,N,N',N'-tetraphenylnaphtylenediamine derivatives, and N,N,N',N'-tetraphenylphenanthrylenediamine derivatives), oxadiazole-based compounds (specific examples include 2,5-di(4-methylaminophenyl)-1,3,4-oxadiazole), styryl compounds (specific examples include 9-(4-diethylaminostyryl)anthracene), carbazole-based compounds (specific examples include polyvinyl carbazole), organic polysilane compounds, pyrazoline-based compound (specific examples include 1-phenyl-3-(p-dimethylaminophenyl)pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. Any one of the hole transport materials listed above may be used independently, or any two or more of the hole transport materials listed above may be used in combination. Of the hole transport materials listed above, a compound represented by chemical formula (H-1) (also referred to below as a compound (H-1)) is preferable.

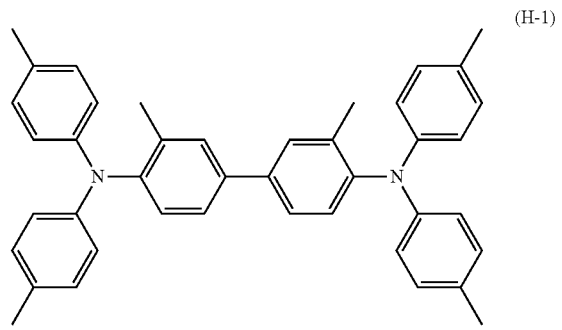 [SMILES: Cc1ccc(N(c2ccc(C)cc2)c2ccc(-c3ccc(N(c4ccc(C)cc4)c4ccc(C)cc4)c(C)c3)cc2C)cc1]

(H-1)

In the case of the multi-layer photosensitive member, the hole transport material is preferably contained in an amount of at least 10 parts by mass and no greater than 200 parts by mass relative to 100 parts by mass of the binder resin contained in the charge transport layer, and more preferably at least 20 parts by mass and no greater than 100 parts by mass.

In the case of the single-layer photosensitive member, the hole transport material is preferably contained in an amount of at least 10 parts by mass and no greater than 200 parts by mass relative to 100 parts by mass of the binder resin contained in the single-layer photosensitive layer, more preferably at least 10 parts by mass and no greater than 100 parts by mass, and particularly preferably at least 10 parts by mass and no greater than 90 parts by mass.

<6. Charge Generating Material>

No particular limitations are placed on the charge generating material other than being a charge generating material that can be used in photosensitive members. Examples of charge generating materials that can be used include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (specific examples include selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridone-based pigments. Any one of the charge generating materials listed above may be used independently, or any two or more of the charge generating materials listed above may be used in combination.

Examples of phthalocyanine-based pigments that can be used include a metal-free phthalocyanine represented by chemical formula (C-1) (also referred to below as a compound (C-1)) and metal phthalocyanine. Examples of metal phthalocyanine that can be used include a titanyl phthalocyanine represented by chemical formula (C-2) (also referred to below as a compound (C-2)), hydroxygallium phthalocyanine, and chlorogallium phthalocyanine. The phthalocyanine-based pigments may be crystalline or non-crystalline. No particular limitations are placed on the crystal structure (for example, α-form, β-form, y-form, v-form, or II-form) of the phthalocyanine-based pigments, and phthalocyanine-based pigments having various different crystal structures may be used.

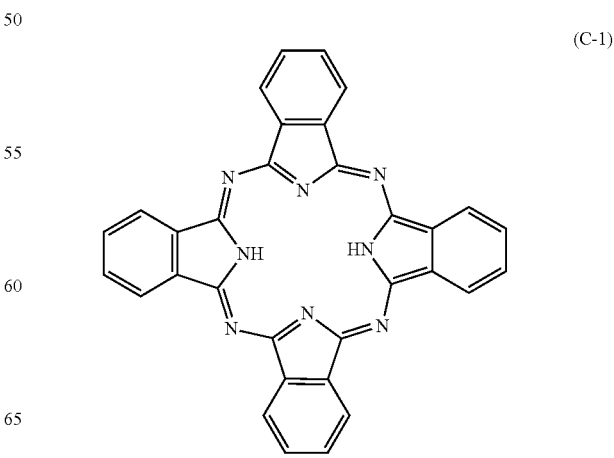

(C-1)

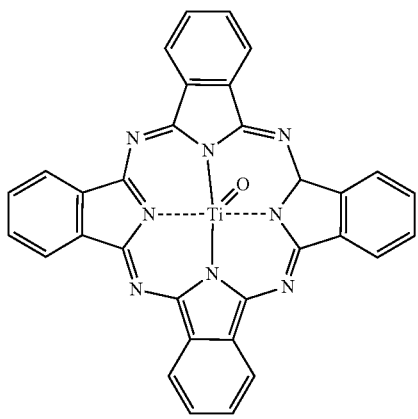

(C-2)

Examples of metal-free phthalocyanine crystals that can be used include metal-free phthalocyanine having an X-form crystal structure (also referred to below as X-form metal-free phthalocyanine). Examples of titanyl phthalocyanine crystals that can be used include titanyl phthalocyanine having an α-form, β-form, or Y-form crystal structure (also referred to below as α-form, β-form, or Y-form titanyl phthalocyanine). Examples of hydroxygallium phthalocyanine crystals that can be used include hydroxygallium phthalocyanine having a V-form crystal structure. Examples of chlorogallium phthalocyanine crystals that can be used include chlorogallium phthalocyanine having a II-form crystal structure.

In a digital optical system image forming apparatus, for example, a photosensitive member that is sensitive to a range of wavelengths that are greater than or equal to 700 nm is preferably used. Examples of such image forming apparatuses include facsimile machines and laser printers including a semiconductor laser. As the charge generating material, phthalocyanine-based pigments are preferable, and metal-free phthalocyanine and titanyl phthalocyanine are more preferable as each having a high quantum yield for a range of wavelengths that are greater than or equal to 700 nm. In order to further improve electrical characteristics of the photosensitive member in which the photosensitive layer contains the quinone derivative (1), (2), or (3), X-form metal-free phthalocyanine or Y-form titanyl phthalocyanine is still more preferable as the charge generating material.

Y-form titanyl phthalocyanine for example exhibits a main peak at a Bragg angle (2θ±0.2°) of 27.2° in a CuKα characteristic X-ray diffraction spectrum. The term "main peak" refers to a peak in the CuKα characteristic X-ray diffraction spectrum having a highest or second highest intensity in a range of Bragg angles (2θ±0.2°) from 3° to 40°.

(Method for Measuring CuKα Characteristic X-ray Diffraction Spectrum)

The following describes an example of a method for measuring the CuKα characteristic X-ray diffraction spectrum. A sample (titanyl phthalocyanine) is loaded into a sample holder of an X-ray diffraction spectrometer (for example, "RINT (registered Japanese trademark) 1100", product of Rigaku Corporation) and an X-ray diffraction spectrum is measured. Measurement is performed using a Cu X-ray tube, a tube voltage of 40 kV, a tube current of 30 mA, and CuKα characteristic X-rays having a wavelength of 1.542 Å. The measurement range (2θ) is from 3° to 40° (start angle: 3°, stop angle: 40°) and the scanning rate is 10°/minute.

A photosensitive member included in an image forming apparatus that includes a short-wavelength laser light source preferably contains an anthanthrone-based pigment as a charge generating material. The short-wavelength laser light for example has a wavelength of at least 350 nm and no greater than 550 nm.

In the case of the multi-layer photosensitive member, the charge generating material is preferably contained in an amount of at least 5 parts by mass an no greater than 1,000 parts by mass relative to 100 parts by mass of the base resin contained in the charge generating layer, and more preferably at least 30 parts by mass and no greater than 500 parts by mass.

In the case of the single-layer photosensitive member, the charge generating material is preferably contained in an amount of at least 0.1 parts by mass and no greater than 50 parts by mass relative to 100 parts by mass of the binder resin contained in the single-layer photosensitive layer, more preferably at least 0.5 parts by mass and no greater than 30 parts by mass, and particularly preferably at least 0.5 parts by mass and no greater than 6.0 parts by mass.

<7. Binder Resin>

Examples of binder resins that can be used include thermoplastic resins, thermosetting resins, and photocurable resins. Examples of thermoplastic resins that can be used include polycarbonate resins, polyarylate resins, styrene-butadiene resins, styrene-acrylonitrile resins, styrene-maleic acid resins, acrylic acid-based resins, styrene-acrylic acid-based resins, polyethylene resins, ethylene-vinyl acetate resins, chlorinated polyethylene resins, polyvinyl chloride resins, polypropylene resins, ionomer resins, vinyl chloride-vinyl acetate resins, alkyd resins, polyamide resins, urethane resins, polysulfone resins, diallyl phthalate resins, ketone resins, polyvinyl butyral resins, polyester resins, and polyether resins. Examples of thermosetting resins that can be used include silicone resins, epoxy resins, phenolic resins, urea resins, and melamine resins. Examples of photocurable resins that can be used include epoxy-acrylic acid-based resins (specific examples include acrylic acid derivative adducts of epoxy compounds) and urethane-acrylic acid-based resins (specific examples include acrylic acid derivative adducts of urethane compounds). Any one of the binder resins listed above may be used independently, or any two or more of the binder resins listed above may be used in combination.

Of the resins listed above, polycarbonate resins are preferable in terms of providing a single-layer photosensitive layer and a charge transport layer that have an excellent balance of workability, mechanical characteristics, optical characteristics, and abrasion resistance. Examples of polycarbonate resins that can be used include bisphenol Z polycarbonate resins having a repeating unit represented by chemical formula (Resin-1) shown below (also referred to below as a polycarbonate resin (Resin-1)), bisphenol ZC polycarbonate resins, bisphenol C polycarbonate resins, and bisphenol A polycarbonate resins.

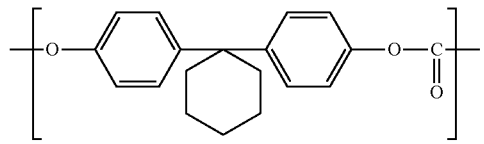

(Resin-1)

The binder resin preferably has a viscosity average molecular weight of at least 40,000, and more preferably at least 40,000 and no greater than 52,500. As a result of the viscosity average molecular weight of the binder resin being at least 40,000, abrasion resistance of the photosensitive member can be improved more easily. As a result of the viscosity average molecular weight of the binder resin being no greater than 52,500, the binder resin has a high tendency to dissolve in a solvent and viscosity of an application liquid for charge transport layer formation or an application liquid for single-layer photosensitive layer formation has a low tendency to be too high during photosensitive layer formation. As a result, the charge transport layer or the single-layer photosensitive layer can be formed easily.

<8. Base Resin>

In the case of the multi-layer photosensitive member, the charge generating layer may contain a base resin. No particular limitations are placed on the base resin other than being a base resin that can be used in photosensitive members. Examples of base resins that can be used include thermoplastic resins, thermosetting resins, and photocurable resins. Examples of thermoplastic resins that can be used include styrene-butadiene-based resins, styrene-acrylonitrile resins, styrene-maleic acid resins, styrene-acrylic acid-based resin, acrylic acid-based resins, polyethylene resins, ethylene-vinyl acetate resins, chlorinated polyethylene resins, polyvinyl chloride resins, polypropylene resins, ionomers, vinyl chloride-vinyl acetate resins, alkyd resins, polyamide resins, urethane resins, polycarbonate resins, polyarylate resins, polysulfone resins, diallyl phthalate resins, ketone resins, polyvinyl butyral resins, polyether resins, and polyester resins. Examples of thermosetting resins that can be used include silicone resins, epoxy resins, phenolic resins, urea resins, melamine resins, and other crosslinkable thermosetting resins. Examples of photocurable resins that can be used include epoxy-acrylic acid-based resins (specific examples include acrylic acid derivative adducts of epoxy compounds) and urethane-acrylic acid-based resins (specific examples include acrylic acid derivative adducts of urethane compounds). Any one of the base resins listed above may be used independently, or any two or more of the base resins listed above may be used in combination.

In general, in order to produce a multi-layer photosensitive member, a charge generating layer is formed on a conductive substrate, and subsequently a charge transport layer is formed on the charge generating layer. An application liquid for charge transport layer formation is applied onto the charge generating layer for the formation of the charge transport layer. Therefore, the base resin contained in the charge generating layer is preferably different from the binder resin contained in the charge transport layer in order to prevent the charge generating layer from dissolving in the solvent of the application liquid for charge transport layer formation.

[2-5. Additive]

The photosensitive layer of the photosensitive member (the charge generating layer, the charge transport layer or the single-layer photosensitive layer) may optionally contain various additives. Examples of additives that can be used include antidegradants (specific examples include antioxidants, radical scavengers, quenchers, and ultraviolet absorbing agents), softeners, surface modifiers, extenders, thickeners, dispersion stabilizers, waxes, donors, surfactants, plasticizers, sensitizers, and leveling agents. Examples of antioxidants that can be used include hindered phenols (specific examples include di(tert-butyl)p-cresol), hindered amines, paraphenylenediamines, arylalkanes, hydroquinone, spirochromanes, spiroindanones, derivatives of any of the above compounds, organosulfur compounds, and organophosphorous compounds.

<10. Intermediate Layer>

The intermediate layer (undercoat layer) for example contains a resin (intermediate layer resin). Provision of the intermediate layer is thought to facilitate flow of current generated when the photosensitive member is exposed to light and inhibit increasing resistance, while also maintaining insulation to a sufficient degree so as to inhibit leakage current from occurring.

Examples of inorganic particles that can be used include particles of metals (specific examples include aluminum, iron, and copper), particles of metal oxides (specific examples include titanium oxide, alumina, zirconium oxide, tin oxide, and zinc oxide), and particles of non-metal oxides (specific examples include silica). Any one of the types of inorganic particles listed above may be used independently, or any two or more of the types of inorganic particles listed above may be used in combination.

No specific limitations are placed on the intermediate layer resin other than being a resin that can be used to form the intermediate layer. The intermediate layer may contain various additives. The additives are the same as defined for the additives for the photosensitive layer.

<11. Method for Producing Photosensitive Member>

In the case of the multi-layer photosensitive member, the multi-layer photosensitive member is for example produced as described below. First, an application liquid for charge generating layer formation and an application liquid for charge transport layer formation are prepared. The application liquid for charge generating layer formation is applied onto a conductive substrate and dried to form a charge generating layer. Next, the application liquid for charge transport layer formation is applied onto the charge generating layer and dried to form a charge transport layer. Through the above, the multi-layer photosensitive member is produced.

The application liquid for charge generating layer formation is prepared by dissolving or dispersing a charge generating material and additive components (for example, a base resin and various additives), depending on necessity thereof, in a solvent. The application liquid for charge transport layer formation is prepared by dissolving or dispersing the quinone derivative (1), (2), or (3) as an electron acceptor compound, a binder resin, a hole transport material, and an additive component (for example, an additive), depending on necessity thereof, in a solvent.

In the case of the single-layer photosensitive member, the single-layer photosensitive member is for example produced as described below. The single-layer photosensitive member is produced by applying an application liquid for single-layer photosensitive layer formation onto a conductive substrate and drying the application liquid for single-layer photosensitive layer formation. The application liquid for single-layer photosensitive layer formation is prepared by dissolving or dispersing a charge generating material, a hole transport material, the quinone derivative (1), (2), or (3) as an electron transport material, a binder resin, and an additive component (for example, an additive), depending on necessity thereof, in a solvent.

No particular limitations are placed on the solvents contained in the application liquid for charge generating layer formation, the application liquid for charge transport layer formation, and the application liquid for single-layer photosensitive layer formation (each of such liquids is also referred to below as an application liquid) other than that the components of the application liquid should be soluble or dispersible in the solvent. Examples of solvents that can be used include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, diethylene glycol dimethyl ether, and propylene glycol monomethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used independently, or any two or more of the solvents listed above may be used in combination. In order to improve workability in production of the photosensitive member, a non-halogenated solvent (i.e., a solvent other than a halogenated hydrocarbon) is preferably used.

Each application liquid is prepared by mixing the components to disperse the components in the solvent. Mixing or dispersion can for example be performed using a bead mill, a roll mill, a ball mill, an attritor, a paint shaker, or an ultrasonic disperser.

The application liquid may for example contain a surfactant in order to improve dispersibility of the components.

No specific limitations are placed on the method by which the application liquid is applied other than being a method that enables uniform application of the application liquid on the conductive substrate. Examples of application methods that can be used include dip coating, spray coating, spin coating, and bar coating.

No particular limitations are placed on the method by which the application liquid is dried other than being a method for evaporating a solvent contained in an application liquid. One specific example of a method involves heat treatment (hot-air drying) using a high-temperature dryer or a reduced pressure dryer. Preferably, the heat treatment is for example performed for at least 3 minutes and no greater than 120 minutes at a temperature of at least 40° C. and no greater than 150° C.

The photosensitive member production method may further include either or both of an intermediate layer formation process and a protective layer formation process as necessary. Appropriate known methods are selected for the intermediate layer formation process and the protective layer formation process.

Through the above, the photosensitive member according to the second embodiment has been described. The photosensitive member according to the second embodiment has excellent electrical characteristics.

EXAMPLES

The following provides more specific description of the present disclosure through use of Examples. However, the present disclosure is not in any way limited by the scope of the Examples.
<1. Materials of Photosensitive Member>
A hole transport material, charge generating materials, and electron transport materials described below were prepared as materials for formation of single-layer photosensitive layers of single-layer photosensitive members.
<1-1. Electron Transport Material>
The quinone derivatives (1-1) to (1-6) and (2-1) were prepared as electron transport materials in accordance with methods described below.

<1-1-1. Preparation of Quinone Derivative (1-1)>
The quinone derivative (1-1) was prepared through a reaction (r-1) shown below.

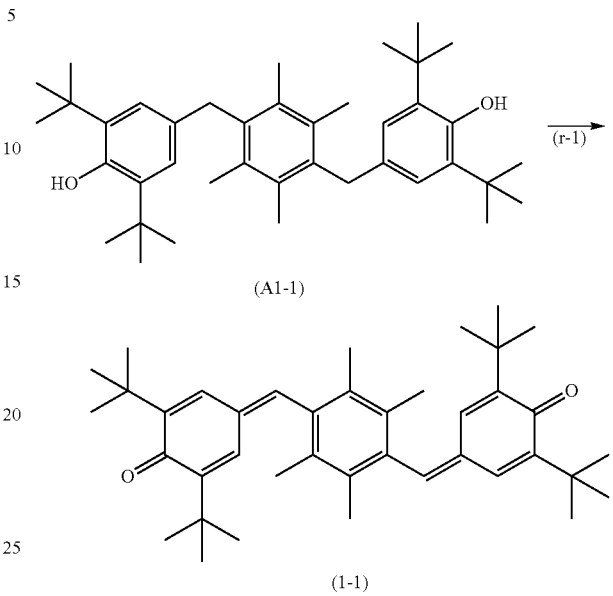

In the reaction (r-1), a phenol derivative represented by chemical formula (A1-1) (also referred to below as a phenol derivative (A1-1)) was oxidized to give the quinone derivative (1-1). More specifically, a 200-mL flask was used as a reaction vessel. Next, 1.71 g (3 mmol) of the phenol derivative (A1-1) and 30 mL of chloroform were added into the reaction vessel to prepare a chloroform solution. Furthermore, potassium permanganate (4.74 g, 30 mmol) was added into the reaction vessel. Next, the content of the reaction vessel was stirred at room temperature (25° C.) for 24 hours. Next, the content of the reaction vessel was filtered to collect a filtrate. The solvent in the filtrate was evaporated. The resultant residue was purified by silica gel column chromatography, using chloroform as a developing solvent. Through the above, the quinone derivative (1-1) was obtained. The quinone derivative (1-1) was yielded in an amount of 0.85 g (in 50 mol % yield).
<1-1-2. Preparation of Quinone Derivatives (1-2) to (1-6)>
The quinone derivatives (1-2) to (1-6) were each prepared according to the same method as the preparation of the quinone derivative (1-1) in all aspects other than the following changes. The number of moles of each of raw materials used in the preparation of the quinone derivatives (1-2) to (1-6) was the same as the number of moles of the corresponding raw material used in the preparation of the quinone derivative (1-1).

Table 1 shows the phenol derivatives (A1) and the quinone derivatives (1) that were used in the reaction (r-1). It should be noted here that the phenol derivatives (A1) are each a reactant in the reaction (r-1). The phenol derivative (A1-1) used in the reaction (r-1) was changed to each of the phenol derivatives (A1) shown in Table 1. As a result, each of the quinone derivatives (1-2) to (1-6) was obtained. Table 1 shows the mass yield and the percentage yield of the quinone derivatives (1).

In Table 1, 1-1, 1-2, 1-3, 1-4, 1-5, and 1-6 in the "Type" column under the quinone derivatives (1) respectively indicate the quinone derivatives (1-1), (1-2), (1-3), (1-4), (1-5), and (1-6). A1-1, A1-2, A1-3, A1-4, A1-5, and A1-6 in the "Type" column under the phenol derivatives (A1) respectively indicate the phenol derivatives (A1-1), (A1-2), (A1-3), (A1-4), (A1-5), and (A1-6). The phenol derivatives (A1-2) to (A1-6) are respectively represented by chemical formulae (A1-2) to (A1-6) shown below.

TABLE 1

| | Reaction (r-1) | | | | |
|---|---|---|---|---|---|
| Phenol derivatives (A1) | | | Quinone derivatives (1) | | |
| Type | Amount [g] | Amount [mmol] | Type | Mass yield [g] | Percentage yield [mol %] |
| A1-1 | 1.71 | 3 | 1-1 | 0.85 | 50 |
| A1-2 | 1.83 | 3 | 1-2 | 0.82 | 45 |
| A1-3 | 1.77 | 3 | 1-3 | 0.80 | 45 |
| A1-4 | 1.20 | 3 | 1-4 | 0.48 | 40 |
| A1-5 | 1.52 | 3 | 1-5 | 0.84 | 55 |
| A1-6 | 1.27 | 3 | 1-6 | 0.64 | 50 |

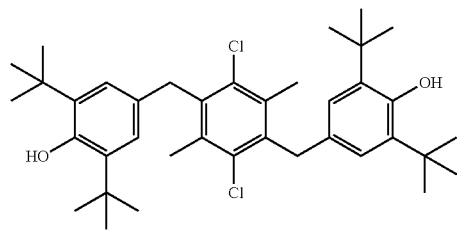

(A1-2)

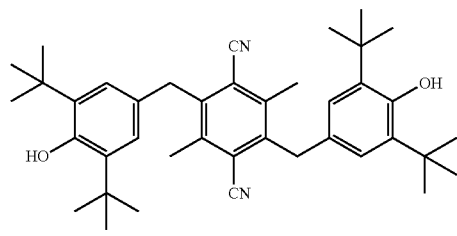

(A1-3)

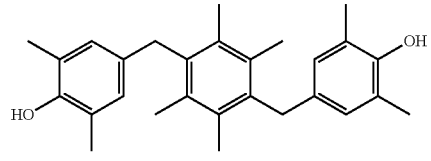

(A1-4)

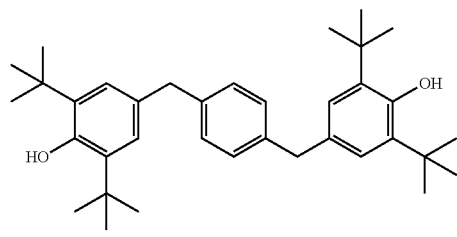

(A1-5)

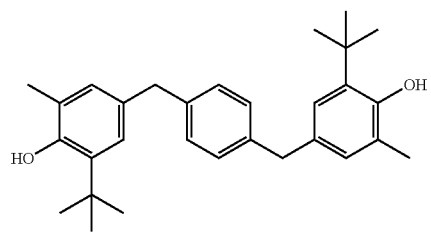

(A1-6)

<1-1-3. Preparation of Quinone Derivative (2-1)>

The quinone derivative (2-1) was prepared through a reaction (r-2) shown below.

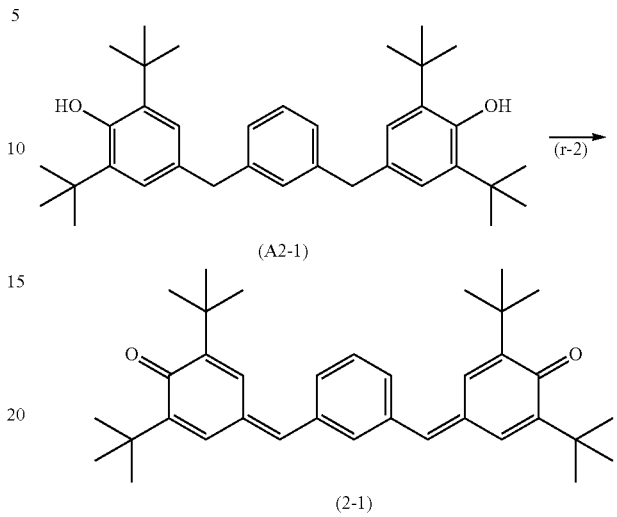

The quinone derivative (2-1) was prepared through the reaction (r-2) according to the same method as the preparation of the quinone derivative (1-1) in all aspects other than that the phenol derivative (A1-1) used in the reaction (r-1) was changed to a phenol derivative (A2-1). The number of moles of each of raw materials used in the preparation of the quinone derivative (2-1) was the same as the number of moles of the corresponding raw material used in the preparation of the quinone derivative (1-1). Table 2 shows the mass yield and the percentage yield of the quinone derivative (2).

In Table 2, 2-1 in the "Type" column under the quinone derivative (2) indicates the quinone derivative (2-1). A2-1 in the "Type" column under the phenol derivative (A2) indicates the phenol derivative (A2-1).

TABLE 2

| | Reaction (r-2) | | | | |
|---|---|---|---|---|---|
| Phenol derivative (A2) | | | Quinone derivative (2) | | |
| Type | Amount [g] | Amount [mmol] | Type | Mass yield [g] | Percentage yield [mol %] |
| A2-1 | 1.52 | 3 | 2-1 | 0.61 | 40 |

Figure 3:
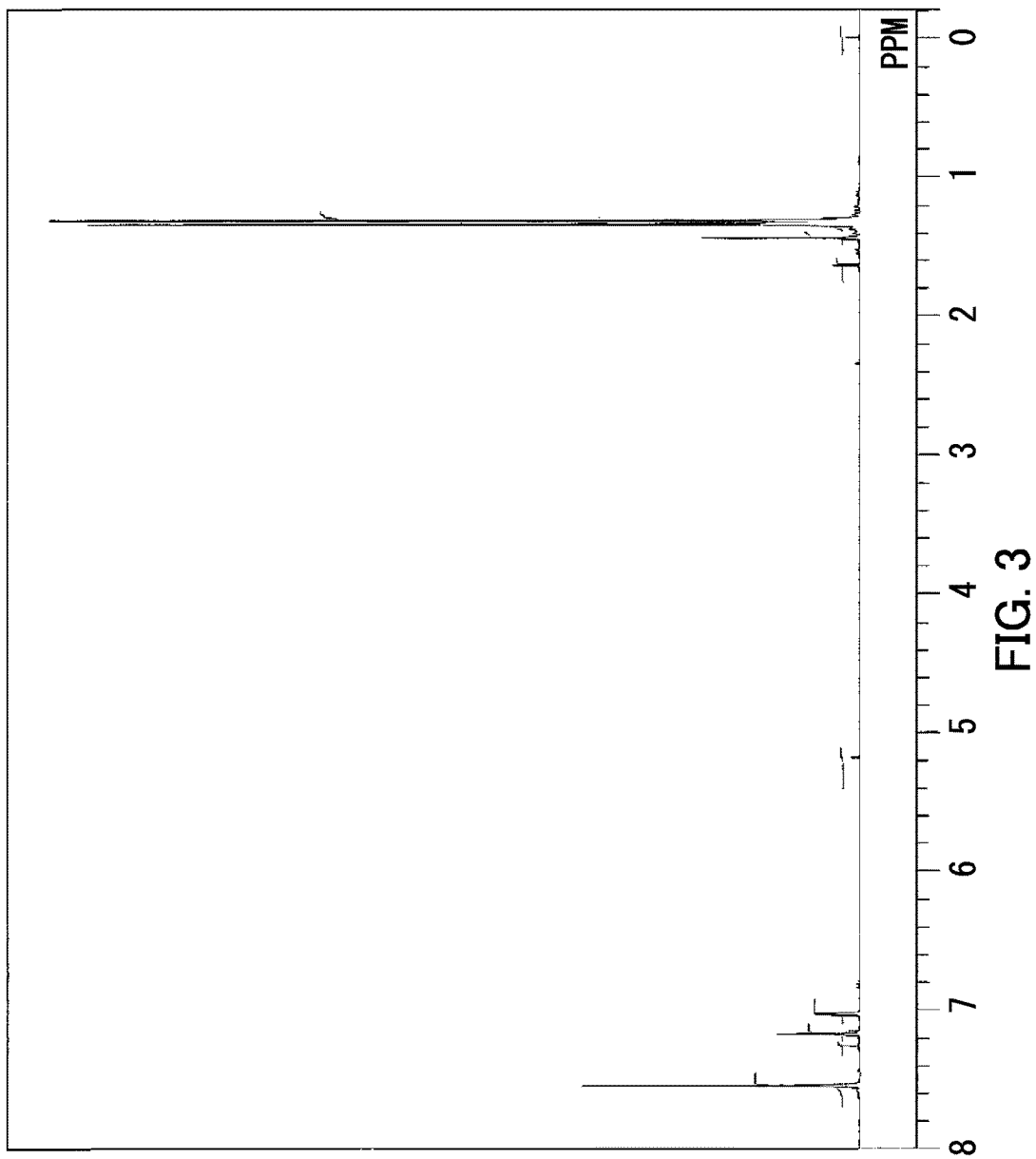
FIG. 3 is a $^1$H-NMR spectrum of a quinone derivative (1-5).
Figure 4:
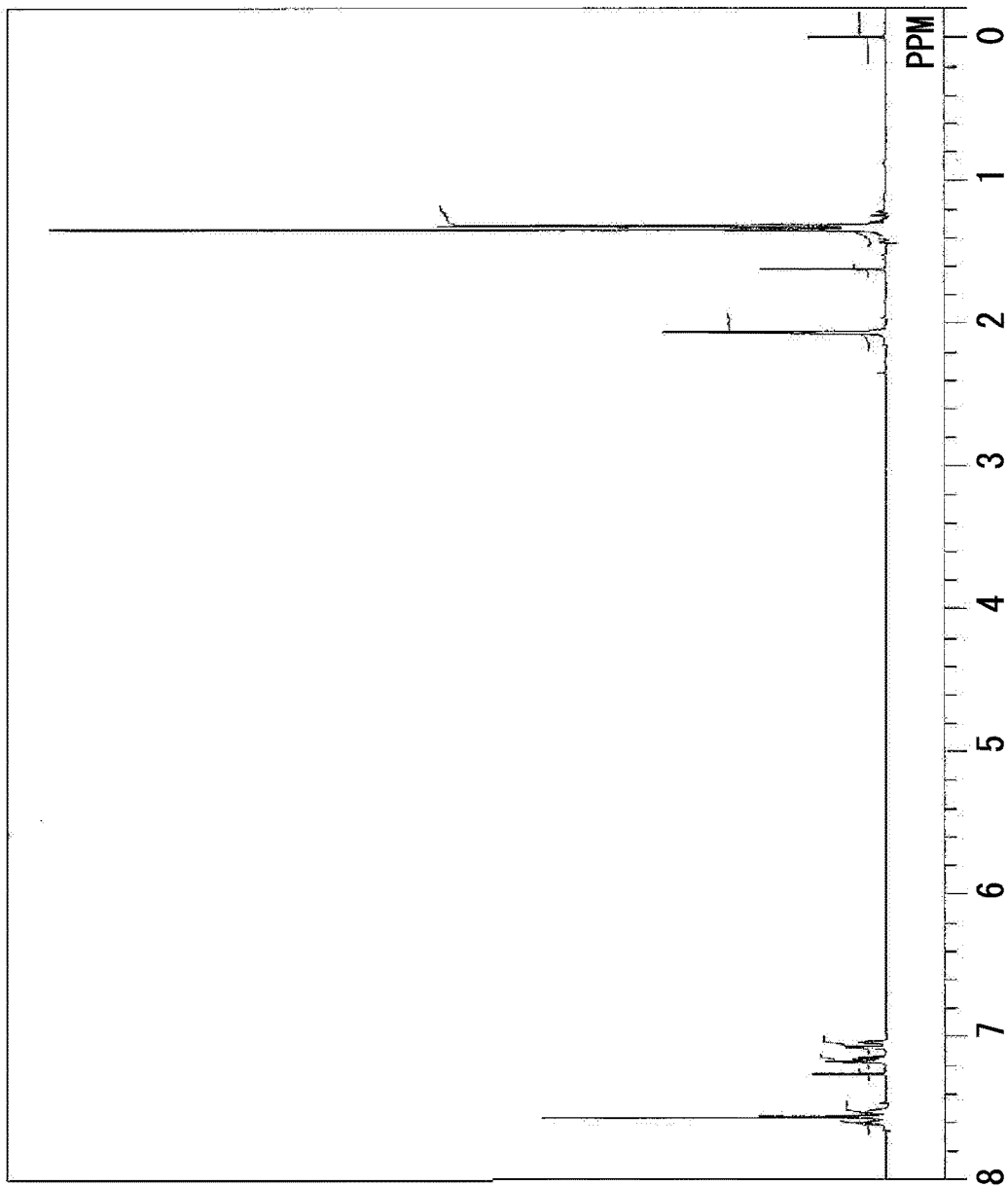
FIG. 4 is a $^1$H-NMR spectrum of a quinone derivative (1-6).
Figure 5:
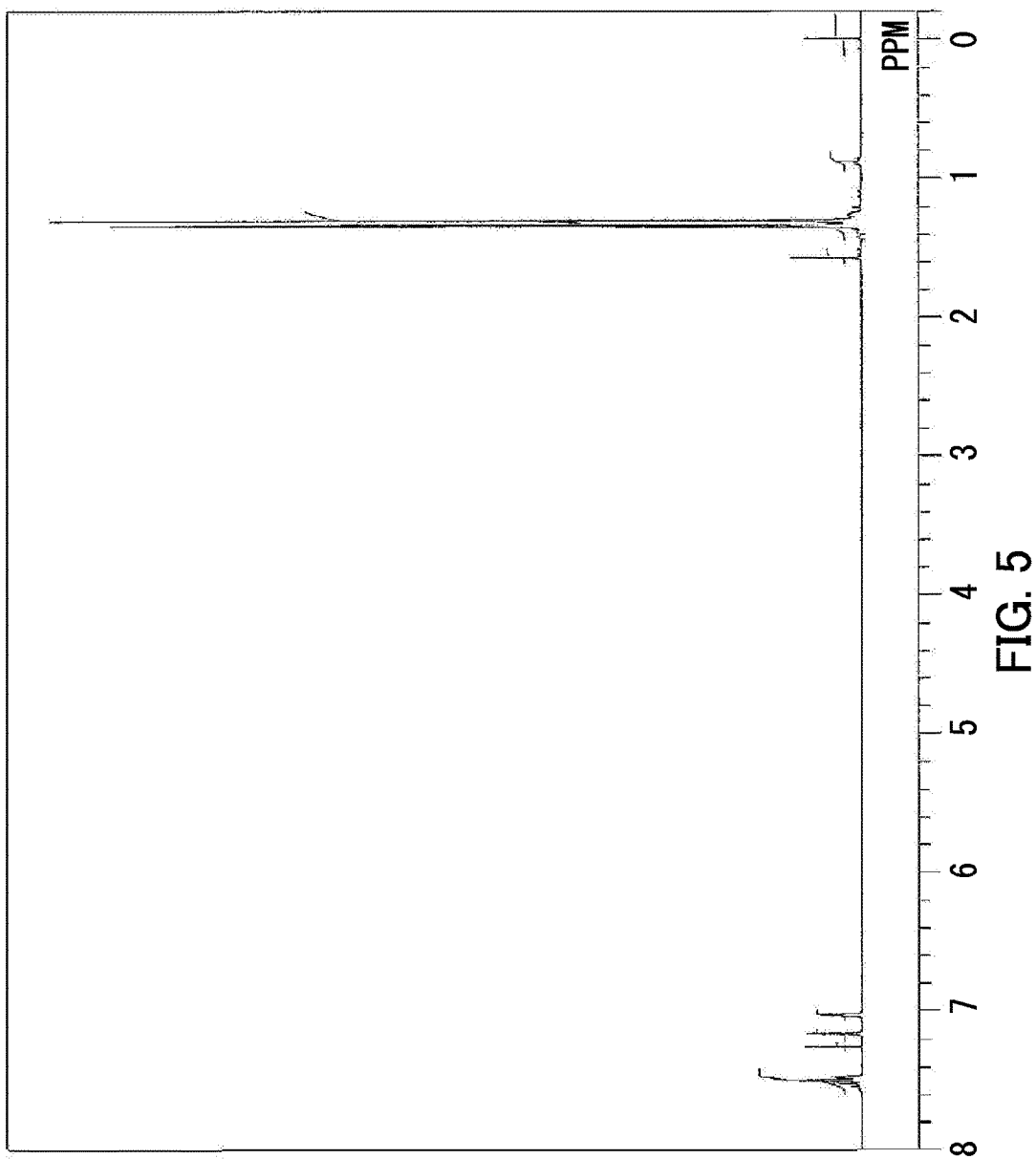
FIG. 5 is a $^1$H-NMR spectrum of a quinone derivative (2-1).

Next, a $^1$H-NMR spectrum of each of the prepared quinone derivatives (1-1) to (1-6) and (2-1) was measured using a proton nuclear magnetic resonance spectrometer (product of JASCO Corporation, 300 MHz). CDCl$_3$ was uses as a solvent. Tetramethylsilane (TMS) was used as an internal standard sample. The quinone derivatives (1-5), (1-6), and (2-1) of all will be taken as representative examples. FIGS. 3, 4, and 5 respectively show $^1$H-NMR spectra of the quinone derivatives (1-5), (1-6), and (2-1). In each of FIGS. 3 to 5, the vertical axis represents signal intensity (unit: arbitrary unit), and the horizontal axis represents chemical shift (unit: ppm). Chemical shifts of the quinone derivatives (1-5), (1-6), and (2-1) are shown below.

Quinone derivative (1-5): $^1$H-NMR (300 MHz, CDCl$_3$) δ=7.55 (s, 6H), 7.18 (s, 2H), 7.03 (d, 2H), 1.35 (s, 18H), 1.32 (s, 18H).

Quinone derivative (1-6): $^1$H-NMR (300 MHz, CDCl$_3$) δ=7.50-7.62 (m, 6H), 7.14-7.18 (m, 2H), 7.04-7.09 (m, 2H), 2.07 (s, 6H), 1.35 (s, 9H), 1.32 (d, 9H).

Quinone derivative (2-1): $^1$H-NMR (300 MHz, CDCl$_3$) δ=7.47-7.55 (m, 6H), 7.17 (s, 2H), 7.03 (d, 2H), 1.35 (s, 18H), 1.31 (s, 18H).

The $^1$H-NMR spectra and the chemical shifts were used to confirm that the quinone derivatives (1-5) to (1-6) and (2-1) were obtained. Likewise, the $^1$H-NMR spectra and chemical shifts of the other quinone derivatives (1-1) to (1-4) were used to confirm that the quinone derivatives (1-1) to (1-4) were obtained.

<1-1-4. Preparation of Compound (E-1)>

The compounds represented by chemical formulae (E-1) and (E-2) (also referred to below as compounds (E-1) and (E-2) respectively) were prepared as electron transport materials.

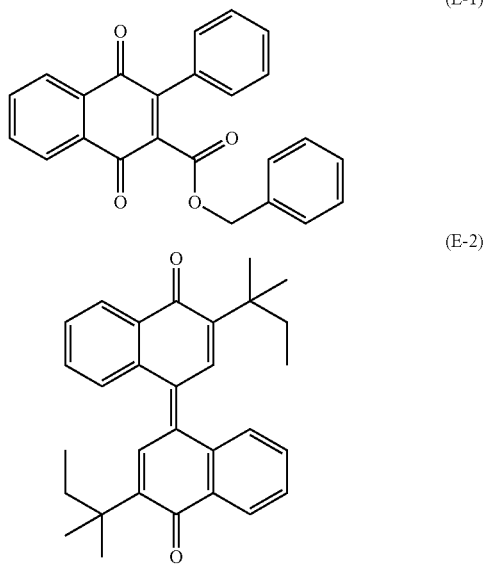

(E-1)

(E-2)

<1-2. Hole Transport Material>

The compound (H-1) described above was prepared as a hole transport material.

<1-3. Charge Generating Material>

The compounds (C-1) to (C-2) described above were prepared as charge generating materials. The compound (C-1) was metal-free phthalocyanine (X-form metal-free phthalocyanine) represented by chemical formula (C-1). The compound (C-1) had an X-form crystal structure.

The compound (C-2) was titanyl phthalocyanine (Y-form titanyl phthalocyanine) represented by chemical formula (C-2). The compound (C-2) had a Y-form crystal structure. The Y-form titanyl phthalocyanine was confirmed to exhibit a main peak at a Bragg angle (2θ±0.2°) of 27.2° in an X-ray diffraction spectrum thereof.

<1-4. Binder Resin>

The polycarbonate resin (Resin-1) ("Panlite (registered Japanese trademark) TS-2050", product of Teijin Limited, viscosity average molecular weight 50,000) described in association with the second embodiment was prepared as a binder resin.

<2. Production of Single-layer Photosensitive Member>

Single-layer photosensitive members (A-1) to (A-14) and single-layer photosensitive members (B-1) to (B-4) were each produced using the materials for the formation of the photosensitive layer thereof.

<2-1. Production of Single-Layer Photosensitive Member (A-1)>

Into a vessel, 5 parts by mass of the compound (C-1) as a charge generating material, 80 parts by mass of the compound (H-1) as a hole transport material, 40 parts by mass of the quinone derivative (1-1) as an electron transport material, 100 parts by mass of the polycarbonate resin (Resin-1) as a binder resin, and 800 parts by mass of tetrahydrofuran as a solvent were added. The contents of the vessel were mixed for 50 hours using a ball mill to disperse the materials in the solvent. Thus, an application liquid for single-layer photosensitive layer formation was obtained. The application liquid for single-layer photosensitive layer formation was applied onto a conductive substrate—an aluminum drum-shaped support (diameter 30 mm, total length 238.5 mm)—by dip coating. The applied application liquid for single-layer photosensitive layer formation was subjected to hot-air drying at 100° C. for 30 minutes. Through the above, a single-layer photosensitive layer (film thickness 30 μm) was formed on the conductive substrate. As a result, the single-layer photosensitive member (A-1) was obtained.

<2-2. Production of Single-Layer Photosensitive Members (A-2) to (A-14) and Single-Layer Photosensitive Members (B-1) to (B-4)>

The single-layer photosensitive members (A-2) to (A-14) and the single-layer photosensitive members (B-1) to (B-4) were each produced according to the same method as the production of the single-layer photosensitive member (A-1) in all aspects other than the following changes. The compound (C-1) used as the charge generating material in the production of the single-layer photosensitive member (A-1) was changed to each of charge generating materials shown in Table 3. The quinone derivative (1-1) used as the electron transport material in the production of the single-layer photosensitive member (A-1) was changed to each of electron transport materials shown in Table 3. Table 3 shows structures of the photosensitive members (A-1) to (A-14) and the photosensitive members (B-1) to (B-4). In Table 3, CGM, HTM, and ETM respectively indicate charge generating material, hole transport material, and electron transport material. In Table 3, x-H$_2$Pc and Y-TiOPc in the "CGM" column respectively indicate X-form metal-free phthalocyanine and Y-form titanyl phthalocyanine. H-1 in the "HTM" column indicates the compound (H-1). In Table 3, 1-1 to 1-6, 2-1, and E-1 to E-2 in the "ETM" column respectively indicate the quinone derivatives (1-1) to (1-6), (2-1) and the compounds (E-1) to (E-2).

<3. Evaluation of Photosensitive Member Properties>

<3-1. Evaluation of Electrical Characteristics of Single-Layer Photosensitive Member>

With respect to each of the single-layer photosensitive members (A-1) to (A-14) and the single-layer photosensitive members (B-1) to (B-4) produced as described above, electrical characteristics of the single-layer photosensitive member were evaluated. The evaluation of the electrical characteristics was carried out under environmental conditions of 23° C. and 60% RH. First, a surface of the single-layer photosensitive member was charged to a positive polarity using a drum sensitivity test device (product of Gen-Tech, Inc.). Charging conditions were a single-layer photosensitive member rotation speed of 31 rpm and an inflow current of +8 μA. The surface potential of the single-layer photosensitive member immediately after charging was set to +700 V. Next, a band pass filter was used to obtain monochromatic light (wavelength 780 nm, half-width 20 nm, light intensity 1.5 μJ/cm$^2$) from white light emitted by a halogen lamp. The thus obtained monochromatic light was irradiated onto the surface of the single-layer photosensitive member. The surface potential of the single-layer photosensitive member was measured once 0.5 seconds had elapsed after completion of the irradiation. The thus measured surface potential was taken to be a post-exposure potential ($V_L$, unit: V). Table 3 shows the thus determined post-exposure potential ($V_L$) of each of the single-layer photosensitive members. It should be noted that the post-exposure potential ($V_L$) having a smaller absolute value indicates that the single-layer photosensitive member has better electrical characteristics.

TABLE 3

| Photosensitive member No. | Photosensitive layer | | | Electrical characteristics |
| --- | --- | --- | --- | --- |
| | CGM | HTM | ETM | $V_L$ (V) |
| Example 1 | A-1 | x—$H_2$Pc | H-1 | 1-1 | +110 |
| Example 2 | A-2 | Y—TiOPc | H-1 | 1-1 | +105 |
| Example 3 | A-3 | x—$H_2$Pc | H-1 | 1-2 | +112 |
| Example 4 | A-4 | Y—TiOPc | H-1 | 1-2 | +107 |
| Example 5 | A-5 | x—$H_2$Pc | H-1 | 1-3 | +114 |
| Example 6 | A-6 | Y—TiOPc | H-1 | 1-3 | +110 |
| Example 7 | A-7 | x—$H_2$Pc | H-1 | 1-4 | +118 |
| Example 8 | A-8 | Y—TiOPc | H-1 | 1-4 | +113 |
| Example 9 | A-9 | x—$H_2$Pc | H-1 | 1-5 | +108 |
| Example 10 | A-10 | Y—TiOPc | H-1 | 1-5 | +104 |
| Example 11 | A-11 | x—$H_2$Pc | H-1 | 1-6 | +108 |
| Example 12 | A-12 | Y—TiOPc | H-1 | 1-6 | +103 |
| Example 13 | A-13 | x—$H_2$Pc | H-1 | 2-1 | +111 |
| Example 14 | A-14 | Y—TiOPc | H-1 | 2-1 | +105 |
| Comparative Example 1 | B-1 | x—$H_2$Pc | H-1 | E-1 | +146 |
| Comparative Example 2 | B-2 | Y—TiOPc | H-1 | E-1 | +127 |
| Comparative Example 3 | B-3 | x—$H_2$Pc | H-1 | E-2 | +124 |
| Comparative Example 4 | B-4 | Y—TiOPc | H-1 | E-2 | +119 |

As shown in Table 3, the photosensitive layer of each of the photosensitive members (A-1) to (A-14) contained any one of the quinone derivatives (1-1) to (1-6) and (2-1) as the electron transport material. The quinone derivatives (1-1) to (1-6) and (2-1) were compounds represented by general formulae (1) and (2). Furthermore, the photosensitive members (A-1) to (A-14) each resulted in a post-exposure potential $V_L$ in a range of from +103 V to +118 V.

As shown in Table 3, the photosensitive layer of each of the photosensitive members (B-1) to (B-4) contained the compound (E-1) or the compound (E-2) as the electron transport material. The compounds (E-1) and (E-2) were not any of the compounds represented by general formulae (1), (2), and (3). Furthermore, the photosensitive members (B-1) to (B-4) each resulted in a post-exposure potential $V_L$ in a range of from +119 V to +146 V.

It is apparent that each of the quinone derivatives (1-1) to (1-6) and (2-1) contained in a photosensitive member improves electrical characteristics of the photosensitive member compared to the compounds (E-1) to (E-2). It is apparent that the photosensitive members (A-1) to (A-14) have superior electrical characteristics to the photosensitive members (B-1) to (B-4).

In consideration of the above results, it is apparent that each of the quinone derivatives represented by general formulae (1), (2), and (3) contained in a photosensitive member improves electrical characteristics of the photosensitive member. That is, it is apparent that the photosensitive member including the photosensitive layer containing the quinone derivative represented by general formula (1), (2), or (3) has excellent electrical characteristics.

What is claimed is:

1. A quinone derivative represented by chemical formula (1-3) shown below:

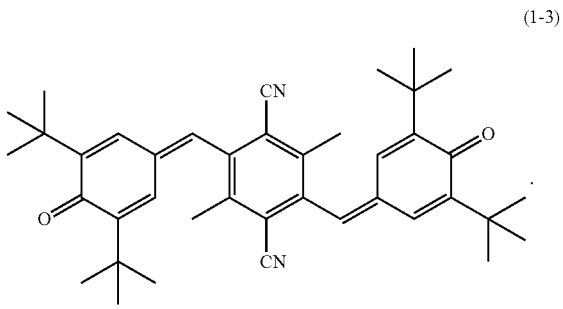 [SMILES: Cc1c(C#N)c(C=C2C=C(C(C)(C)C)C(=O)C(C(C)(C)C)=C2)c(C)c(C#N)c1C=C1C=C(C(C)(C)C)C(=O)C(C(C)(C)C)=C1]

(1-3)

2. An electrophotographic photosensitive member comprising a conductive substrate and a photosensitive layer, wherein
the photosensitive layer contains a charge generating material, a hole transport material, the quinone derivative according to claim 1, and a binder resin.

3. The electrophotographic photosensitive member according to claim 2, wherein
the photosensitive layer is a single-layer photosensitive layer.

4. The electrophotographic photosensitive member according to claim 2, wherein
the charge generating material includes X-form metal-free phthalocyanine or Y-form titanyl phthalocyanine.

5. The electrophotographic photosensitive member according to claim 2, wherein
the hole transport material includes a compound represented by chemical formula (H-1) shown below:

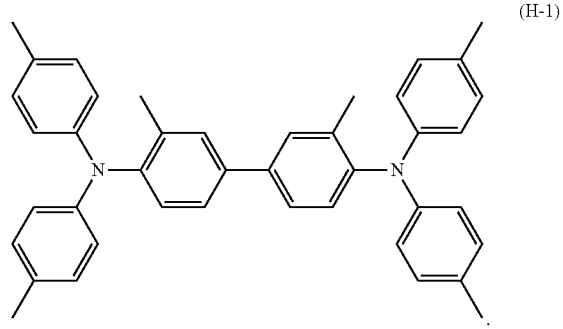 [SMILES: Cc1ccc(N(c2ccc(C)cc2)c2ccc(-c3ccc(N(c4ccc(C)cc4)c4ccc(C)cc4)c(C)c3)cc2C)cc1]

(H-1)

* * * * *